(12) United States Patent
Rudi et al.

(10) Patent No.: US 7,560,228 B2
(45) Date of Patent: *Jul. 14, 2009

(54) SOLID-PHASE NUCLEIC ACID ISOLATION

(75) Inventors: Knut Rudi, Oslo (NO); Kjetill Sigurd Jakobsen, Oslo (NO)

(73) Assignee: Genpoint A/S, Oslo (NO)

( * ) Notice: Subject to any disclaimer, the term of this patent is extended or adjusted under 35 U.S.C. 154(b) by 422 days.

This patent is subject to a terminal disclaimer.

(21) Appl. No.: 10/458,913

(22) Filed: Jun. 11, 2003

(65) Prior Publication Data

US 2004/0072215 A1 Apr. 15, 2004

Related U.S. Application Data

(63) Continuation of application No. 09/423,796, filed as application No. PCT/GB98/01358 on May 13, 1998, now Pat. No. 6,617,105.

(30) Foreign Application Priority Data

May 13, 1997 (GB) ................................. 9709728.1

(51) Int. Cl.
*C12Q 1/68* (2006.01)
*C12N 1/08* (2006.01)
*C07H 1/08* (2006.01)

(52) U.S. Cl. ........................... 435/6; 435/270; 435/259; 536/127

(58) Field of Classification Search ........................ None
See application file for complete search history.

(56) References Cited

U.S. PATENT DOCUMENTS

| 4,001,197 A | 1/1977 | Mitchell et al. |
| 5,652,141 A | 7/1997 | Henco |
| 6,020,186 A | 2/2000 | Henco et al. |
| 2002/0137920 A1 | 9/2002 | Kleiber et al. |

FOREIGN PATENT DOCUMENTS

| EP | 0 366 448 A2 | 5/1990 |
| EP | 0 389 063 | 9/1990 |
| EP | 0 402 997 A2 | 12/1990 |
| EP | 0 605 003 | 7/1994 |
| WO | WO 91/08308 | 6/1991 |
| WO | WO 91/12079 | 8/1991 |
| WO | WO 92/07863 | 5/1992 |
| WO | WO 92/17609 | 10/1992 |
| WO | WO 96/18731 | 6/1996 |
| WO | WO 97/09600 | 4/1997 |

OTHER PUBLICATIONS

Metzler et al. (1996) Mitt. Gebiete Lebensm.Myg. 87, 55-72 (reproduction of presentation held in Zurich Nov. 23, 1995 [and translation thereof].
Kristensen et al. (1997) Nucleic Acid Res. 15, 5507-5516.
Hou et al. (1980) Appl. Environm. Microbiol., 40, 892-896.
Farrah et al. (1991) Appl. Environm. Microbiol., 57, 2502-2506.
Goyal et al. (1980) Appl. Environm. Microbiol., 39, 85-91.
U.S. EPA Manual of Methods of Biology, 1984, Chapter 7.
Britton et al., Water Research 8, 549-551 (1974).
Birnboim et al. (1979) Nucleic Acids Research 7(6), 1513-1523.
Birnboim (1983) Methods of Enzymology, 100, 243-255.
Toranzos et al. (1992) Canadian Journal of Microbiology, 38, 365-369.
Farrah et al. (1977) Applied and Environmental Microbiology, 33(5) 1192-1196.
Gerba et al. (1978) Applied and Environmental Microbiology, 35(3), 540-548.
Karlik et al. (1980) Biochemistry, 19, 5991-5998.
Piña et al. (1996) BioMetals, 9, 311-316.
Dyrssen et al. (1987) Journal of Inorganic Biochemistry, 29, 67-75.
Wedrychowski et al. (1986) Journal of Biological Chemistry, 261(7), 3370-3376.
Rao et al. (1993) Biochemica et Biophysica Acta, 1172, 17-20.
Wadowsky et al. (1994) Journal of Clinical Microbiology, 32(4), 1054-1057.
Johnson et al. (1995) Applied and Environmental Microbiology, 61(11), 3849-3855.
Boom et al. (1990), "Rapid and Simple Method for Purification of Nucleic Acids," Journal of Clinical Microbiology, 28:495-503.
Cook (1984), "A General Method for Preparing Intact Nuclear DNA," The EMBO Journal, 3:1837-1842.
Davies et al. (1994), "Magnetic Solid Phase Supports for Affinity Purification of Nucleic Acids" in Special Publications of the Royal Society for Chemistry, Separations for Biotechnology, 158:152-158.
Deggerdal et al. (1997), "Rapid Isolation of PCR-Ready DNA from Blood, Bone Marrow and Cultured Cells, Based on Paramagnetic Beads," Bio Techniques, 22:554-557.
Jackson et al. (1985), "A General Method for Preparing Chromatin Containing Intact DNA,"The EMBO Journal, 4:913-918.
Leadon et al. (1982), "A Rapid and Mild Procedure for the Isolation of DNA from Mammalian Cells," Analytical Biochemistry, 120:282-288.
Stratagene Catalog, 1988, p. 39.

*Primary Examiner*—Juliet C Switzer
(74) *Attorney, Agent, or Firm*—Crowell & Moring LLP

(57) ABSTRACT

The present invention provides a method of isolating nucleic acid from a sample of cells, said method comprising: (a) binding cells in said sample in a solid support to isolate cells from the sample; (b) lysing the isolated cells; and (c) binding nucleic acid released from said lysed cells to said same solid support and a kit for carrying out such a method. The method may advantageously be used to prepare nucleic acid for use in a nucleic acid-based target cell detection method.

15 Claims, 1 Drawing Sheet

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer CW

<400> SEQUENCE: 1
cgtagcttcc ggtggtatcc acgt                                          24

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide primer DF
<220> FEATURE:
<221> NAME/KEY: variation
<222> LOCATION: (16)...(16)
<223> OTHER INFORMATION: n is a, t, c or g

<400> SEQUENCE: 2
gggcaryttc cacakngtcc a                                             21

SOLID-PHASE NUCLEIC ACID ISOLATION

CROSS-REFERENCE TO RELATED APPLICATION

Figure 1:
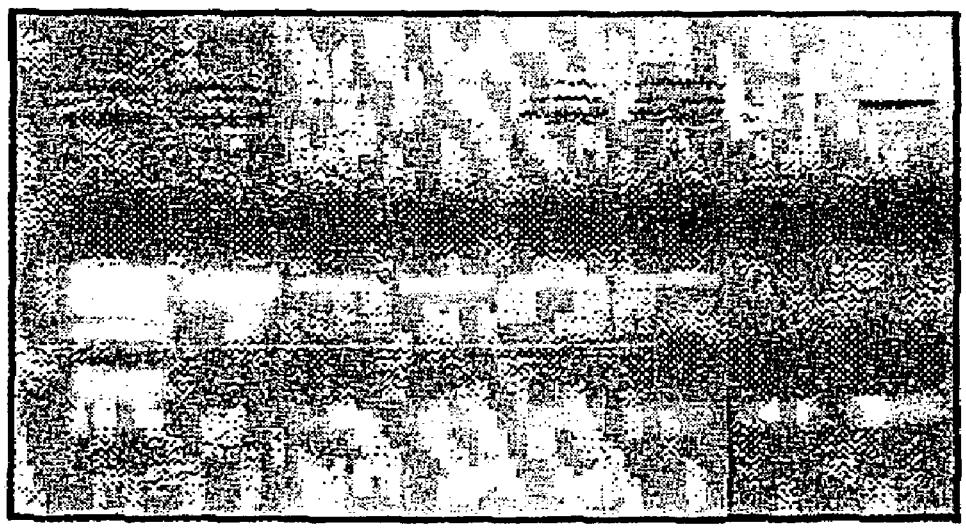

This application is a continuation of U.S. application Ser. No. 09/423,796, filed Feb. 7, 2000 now U.S. Pat. No. 6,617,105, which is a § 371 of PCT/GB98/01358, filed May 13, 1998 and the disclosure of which is incorporated herein by reference.

The present invention relates to the isolation of nucleic acid, and especially to a method for isolating DNA from cells which combines a solid phase cell isolation step with a solid phase DNA isolation step.

The isolation of nucleic acid is an important step in many biochemical and diagnostic procedures. For example, the separation of nucleic acids from the complex mixtures in which they are often found is frequently necessary before other studies and procedures eg. detection, cloning, sequencing, amplification, hybridisation, cDNA synthesis etc. can be undertaken; the presence of large amounts of cellular or other contaminating material eg. proteins or carbohydrates, in such complex mixtures often impedes many of the reactions and techniques used in molecular biology. In addition, DNA may contaminate RNA preparations and vice versa. Thus, methods for the isolation of nucleic acids from complex mixtures such as cells, tissues etc. are demanded, not only from the preparative point of view, but also in the many methods in use today which rely on the identification of DNA or RNA eg. diagnosis of microbial infections, forensic science, tissue and blood typing, detection of genetic variations etc.

The use of DNA or RNA identification is now widely accepted as a means of distinguishing between different cells or cell types or between variants of the same cell type containing DNA mutations. Thus, HLA typing, which is more commonly carried out by identification of characteristic surface antigens using antibodies, may alternatively be effected by identification of the DNA coding for such antigens. Microbial infection or contamination may be identified by nucleic acid analysis to detect the target organism, rather than relying on detecting characterising features of the cells of the microorganisms eg. by morphological or biochemical. Genetic variations may be identified by similar means.

In general, DNA or RNA is identified by hybridisation to one or more oligonucleotides under conditions of stringency sufficient to ensure a low level of non specific binding. Commonly, the hybridising nucleotides are used in pairs as primers in the various forms of in vitro amplification now available, primarily the polymerase chain reaction (PCR), but also the Ligase Amplification Reaction (LAR), the Self-Sustained Sequence Replication (3SR) and the Q-beta replicase amplification system. After amplification the DNA may be further characterised by sequencing, eg. by the Sanger method. Amplification and sequencing may be combined.

As mentioned above, all methods generally require an initial nucleic acid isolation step, to separate the nucleic acid from materials eg. protein which may interfere in the hybridisation and amplification techniques which are used.

A range of methods are known for the isolation of nucleic acids, but generally speaking, these rely on a complex series of extraction and washing steps and are time consuming and laborious to perform.

Classical methods for the isolation of nucleic acids from complex starting materials such as blood or blood products or tissues involves lysis of the biological material by a detergent or chaotrope, possibly in the presence of protein degrading enzymes, followed by several extractions with organic solvents eg. phenol and/or chloroform, ethanol precipitation, centrifugations and dialysis of the nucleic acids. Not only are such methods cumbersome and time consuming to perform, but the relatively large number of steps required increases the risk of degradation, sample loss or cross-contamination of samples where several samples are simultaneously processed.

Improvements in methods for isolating nucleic acids are thus continually being sought, and more recently, other methods have been proposed which rely upon the use of a solid phase. In U.S. Pat. No. 5,234,809, for example, is described a method where nucleic acids are bound to a solid phase in the form of silica particles, in the presence of a chaotropic agent such as a guanidinium salt, and thereby separated from the remainder of the sample. WO 91/12079 describes a method whereby nucleic acid is trapped on the surface of a solid phase by precipitation. Generally speaking, alcohols and salts are used as precipitants.

Whilst such methods speed up the nucleic acid separation process, a need still exists for methods which are quick and simple to perform, which enable good yields to be obtained without losses, and in particular which are readily amenable to isolating nucleic acids from cells in mixtures or environments where they may be present at low concentrations, as a preparative first step in isolating nucleic acids from target cells in nucleic-acid based cell detection procedures. The present invention addresses this need. In particular, whilst hybridisation-based techniques such as PCR and other nucleic acid-based methods for detecting microorganisms allow high sensitivity detection of cells in samples, sample preparation ie. the concentration of the target cells and nucleic acid purification, are crucial factors in achieving the high sensitivity and. reproducibility of the method. At present, cells are commonly first isolated from the sample by filtration, centrifugation or affinity binding to antibodies attached to a solid phase. After cell concentration in this manner, the DNA is then purified from the concentrated cells, often by classical phenol/chloroform extraction methods as discussed above, with their attendant disadvantages.

We now propose a novel approach to this problem which integrates cell isolation and nucleic acid purification in a single "step", by using the same solid phase for both cell adsorption and nucleic acid purification. This is achieved by binding the cells to a solid support as a first step. The same solid support is then used under conditions that lyse the bound cells, and then which enable the nucleic acid to bind to the support.

In this manner nucleic acid may be isolated from a sample in a form suitable for amplification or other downstream processes, by a simple and quick to perform procedure which may take less than 45 minutes.

In one aspect, the present invention thus provides a method of isolating nucleic acid from a sample of cells, said method comprising:

(a) binding cells in said sample to a solid support to isolate cells from the sample;

(b) lysing the isolated cells; and (c) binding nucleic acid released from said lysed cells to said same solid support.

The nucleic acid may be DNA, RNA or any naturally occurring or synthetic modification thereof, and combinations thereof. Preferably however the nucleic acid will be DNA, which may be single or double stranded or in any other form, eg. linear or circular.

The term "cell" is used herein to include all prokaryotic (including archaebacteria) and eukaryotic cells and other viable entities such as viruses and mycoplasmas, and subcellular components such as organelles. Representative "cells" thus include all types of mammalian and non-mammalian animal cells, plant cells, protoplasts, bacteria, protozoa and viruses.

The sample may thus be any material containing nucleic acid within such cells, including for example foods and allied products, clinical and environmental samples. Thus, the sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma or buffy coat, urine, faeces, cerebrospinal fluid or any other body fluids, tissues, cell cultures, cell suspensions etc., and also environmental samples such as soil, water, or food samples.

The sample may also include relatively pure or partially purified starting materials, such as semi-pure preparations obtained by other cell separation processes.

Binding of the cells to the solid support may be achieved in any known or convenient manner. For example, non-specific binding of the cells to the support may be achieved by appropriate choice of the solid support and conditions eg. the chemical or physical nature of the surface of the solid support, (eg. hydrophobicity or charge), the pH or composition of the isolation medium etc. The nature of the target cells may also play a role and it has, for example, been shown that certain hydrophobic cells may readily bind non-specifically to hydrophobic surfaces, whereas hydrophilic cells may bind to more hydrophilic surfaces. Negatively charged cells such as B-lymphocytes have also been observed to have a high degree of non-specific binding to weakly-positively charged surfaces. Thus solid supports having appropriately charged surfaces for binding of a desired cell type may be used. Appropriate buffers etc. may be used as media for the cell isolation step to achieve conditions appropriate for cell binding, simply bringing the solid support and the sample into contact in an appropriate medium. Conveniently, a buffer of appropriate charge, osmolarity etc. may be added to the sample prior to, simultaneously with, or after contact with the solid support.

Advantageously, non-specific binding of cells may be achieved according to the invention by precipitating the cells onto the support using a precipitant, for example by contacting the cells with the support in the presence of alcohol and salt, eg. by adding to the sample, a buffer containing alcohol and salt. The use of alcohol and salt in separation and purification procedures such as precipitation is commonplace and any suitable alcohol or salt used in such procedures, may be used according to the present invention. Thus, conveniently the alcohol may be any alkanol, and lower alkanols such as isopropanol and ethanol have been found to be suitable. Other suitable alcohols include methanol and n-butanol.

The salt may be provided by any convenient source eg. sodium or potassium chloride or acetate, or ammonium acetate. Appropriate concentrations of alcohol and salt may be determined according to the precise system and reagents used. Generally speaking addition of 0.5 to 3 volumes of alcohol eg. 1 volume, to the sample has been found to be suitable. Conveniently the alcohol may be used at concentrations of 50-100% (w/v). The use of salt concentrations of eg. 0.1 to 10.0 M, more particularly 0.1 to 7.0 M, e.g. 0.1 to 3.0 M has been found to be suitable, and conveniently the salt may be included, at the above concentrations in the alcohol solution. Thus, a so-called "cell-binding buffer" may be used containing the alcohol and salt at the desired concentrations. Alternatively, the salt and alcohol may be added separately.

The use of alcohol as precipitant for the cells according to the invention is advantageous for use of the method in clinical diagnostic procedures, since the use of alcohol to conserve clinical samples is common. Thus, patient samples may simply be added to an alcohol-containing cell-binding buffer, whereby the samples are conserved and ready for purification of the nucleic acid.

As an alternative to precipitation with salt/alcohol, other precipitants may be used, for example polyethylene glycols (PEGs) or other high molecular weight polymers with similar properties, either alone or in combination with salt and/or alcohol. The concentrations of such polymers may vary depending upon the precise system eg. polymer and cell type, but generally concentrations from 1 to 50% (w/v), eg. 2-30% may be used.

Cells with phagocytic activity may be captured by their ability to "bind" or "swallow" a particulate solid phase eg. beads, and thereby can readily be collected. In this case, the cell-containing sample needs simply to be contacted or incubated with the solid phase under appropriate conditions. This kind of cell capture is not dependent on specific binding.

The solid support may also be provided with moieties which assist in the non-specific binding of cells, for example proteins or protein fragments or polypeptides which are bound non-specifically by cells. Thus, for example, a solid support coated with or carrying antibodies will bind cells non-specifically through Fc receptors on the cell surface. Techniques for immobilising antibodies and other proteins or polypeptides on solid surfaces are well known in the art.

Finally, as mentioned above, non-specific cell-binding to solid supports having charged, hydrophobic or hydrophilic surfaces may be achieved by using buffers, often in combination with salt, to achieve pH conditions appropriate for binding. The precise buffers and conditions will vary depending on the type of cell, solid support etc.

The various components are mixed and simply allowed to stand for a suitable interval of time to allow the cells to bind to the support. The support may then be removed from the solution by any convenient means, which will depend of course on the nature of the support, and includes all forms of withdrawing the support away from the sample supernatant, or vice versa, for example centrifugation, decanting, pipetting etc.

The conditions during this process are not critical, and it has been found convenient, for example, simply to mix the sample with the "cell-binding buffer" in the presence of a solid phase, and allow it to stand at room temperature, eg. for 5 to 30 minutes, eg. 20 minutes before separating. As mentioned above, the reaction time is not critical and as little as 5 minutes may be often enough. However, if convenient, longer periods may be used, eg. 20 minutes to 3 hours, or even overnight. Mixing can be done by any convenient means, including for example simple agitation by stirring or vortexing. Also, if desired, higher or lower temperatures may be used, but are not necessary.

Other optional components in the "cell-binding" composition include high molecular weight polymers eg. PEGs etc., weak uncharged detergents eg. Triton X-100, NP-40 etc, DNAses and other enzymes, as long as they leave the cells intact.

Preferred "cell-binding" compositions may, for example, comprise:
  isopropanol, 0.75 M ammonium acetate
  75% ethanol, 0.75 M ammonium acetate.

Although non-specific binding of cells is preferred according to the invention, it is also possible to use solid supports which have been modified to permit the selective capture of desired cells containing the nucleic acid. Thus for example, supports carrying antibodies, or other binding proteins eg. lectins, specific for a desired cell type may be used. This may introduce a degree of selectivity to the isolation of the nucleic acid, since only nucleic acid from a desired target source within a complex mixture may be separated. Thus for example, such a support may be used to separate and remove the desired target cell type etc. from the sample.

The preparation of such selective cell capture matrices is well known in the art and described in the literature.

The solid support may be any of the well known supports or matrices which are currently widely used or proposed for immobilisation, separation etc. These may take the form of particles, sheets, gels, filters, membranes, fibres, capillaries, or microtitre strips, tubes, plates or wells etc.

Conveniently the support may be made of glass, silica, latex or a polymeric material. Preferred are materials presenting a high surface area for binding of the cells, and subsequently, of the nucleic acid. Such supports will generally have an irregular surface and may be for example be porous or particulate eg. particles, fibres, webs, sinters or sieves. Particulate materials eg. beads are generally preferred due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10 and more preferably not more than 6 µm. For example, beads of diameter 2.8 µm and 4.5 µm have been shown to work well.

Monodisperse particles, that is those which are substantially uniform in size (eg. size having a diameter standard deviation of less than 5%) have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dyno Particles AS (Lillestrøm, Norway) as well as from Qiagen, Pharmacia and Serotec.

However, to aid manipulation and separation, magnetic beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick; simple and efficient way of separating the particles following the cell and nucleic acid binding steps, and is a far less rigorous method than traditional techniques such as centrifugation which generate shear forces which may disrupt cells or degrade nucleic acids.

Thus, using the method of the invention, the magnetic particles with cells attached may be removed onto a suitable surface by application of a magnetic field eg. using a permanent magnet. It is usually sufficient to apply a magnet to the side of the vessel containing the sample mixture to aggregate the particles to the wall of the vessel and to pour away the remainder of the sample.

Especially preferred are superparamagnetic particles for example those described by Sintef in EP-A-106873, as magnetic aggregation and clumping of the particles during reaction can be avoided, thus ensuring uniform and nucleic acid extraction. The well-known magnetic particles sold by Dynal AS (Oslo, Norway) as DYNABEADS, are particularly suited to use in the present invention.

Functionalised coated particles for use in the present invention may be prepared by modification of the beads according to U.S. Pat. Nos. 4,336,173, 4,459,378 and 4,654,267. Thus, beads, or other supports, may be prepared having different types of functionalised surface, for example positively or negatively charged, hydrophilic or hydrophobic.

Different cells exhibit different degrees of non-specific binding to different surfaces and supports and it may be advantageous to "titrate" the amount of the solid support (eg. the number of particles) per volume unit, in order to optimise the cell-binding conditions, and determine the optimum support area, eg. particle concentration for a given system.

Following cell binding, the isolated or support-bound cells are lysed to release their nucleic acid. Methods of cell lysis are well known in the art and widely described in the literature and any of the known methods may be used. Different methods may be more appropriate for different cells, but any of the following methods could, for example, be used: detergent lysis using eg. SDS, LiDS or sarkosyl in appropriate buffers; the use of chaotropes such as Guanidium Hydrochloride (GHCl), Guanidium thiocyanate (GTC), sodium iodide (NaI), perchlorate etc; mechanical disruption, such as by a French press, sonication, grinding with glass beads, alumina or in liquid nitrogen; enzymatic lysis, for example using lysozyme, proteinases, pronases or cellulases or any of the other lysis enzymes commercially available; lysis of cells by bacteriophage or virus infection; freeze drying; osmotic shock; microwave treatment; temperature treatment; eg. by heating or boiling, or freezing, eg. in dry ice or liquid nitrogen, and thawing; alkaline lysis. As mentioned above, all such methods are standard lysis techniques and are well known in the art, and any such method or combination of methods may be used.

Conveniently, lysis may be achieved according to the present invention by using chaotropes and/or detergents. For example, in the case of bacterial cells, the combination of a chaotrope with a detergent has been found to be particularly effective. An exemplary suitable lysis agent thus includes a chaotrope such as GTC or GHCl and a detergent such as SDS or Sarkosyl. The lysis agents may be supplied in simple aqueous solution, or they may be included in a buffer solution, to form a so-called "lysis buffer". Any suitable buffer may be used, including for example Tris, Bicine, Tricine and phosphate buffers. Alternatively the lysis agents may be added separately. Suitable concentrations and amounts of lysis agents will vary according to the precise system, nature of the calls etc. and may be appropriately determined, but concentrations of eg. 2M to 7M chaotropes such as GTC GHCl, NaI or perchlorate may be used, 0.1M to 1M alkaline agents such as NaOH, and 0.1 to 50% (w/v) eg. 0.5 to 15% detergent. Thus, an example of a suitable representative lysis buffer includes an aqueous solution of 4M GTC, 1% (w/v) sarkosyl.

To carry out the method of the invention, the isolated, support-bound cells, may conveniently be removed or separated from the remainder of the sample, thereby concentrating or enriching the cells. Thus the cell binding step serves to enrich the cells or to concentrate them in a smaller volume than the initial sample. Lysis then may conveniently be achieved by adding an appropriate lysis buffer containing the desired lysis agents or by subjecting the isolated cells to the desired lysis conditions. For example, in the case of simply adding a lysis buffer containing appropriate lysis agents, the isolated cells may simply be incubated in the presence of the lysis buffer for a suitable interval to allow lysis to take place. Different incubation conditions may be appropriate for different lysis systems, and are known in the art. For example for a detergent and/or chaotrope containing lysis buffer, incubation may take place at room temperature or at higher temperatures eg. 37° C. or 65° C. Likewise, time of incubation may be varied from a few minutes eg. 5 or 10 minutes to hours, eg. 1 to 2 hours. In the case of GTC/sarkosyl lysis buffers and bacterial cells, incubation at eg. 65° C. for 10-20 minutes has been found to be appropriate, but this may of course be varied according to need. For enzymatic lysis, eg. using proteinase K etc, longer treatment times may be required, eg. overnight.

Following lysis, the released nucleic acid is bound to the same support to which the lysed cells are bound. This nucleic acid binding may be achieved in any way known in the art for binding nucleic acid to a solid support. Conveniently, the nucleic acid is bound non-specifically to the support ie. independently of sequence. Thus, for example the released nucleic acid may be precipitated onto the support using any of the known precipitants for nucleic acid, eg. alcohols, alcohol/salt combinations, polyethylene glycols (PEGs) etc. Precipitation of nucleic acids onto beads in this manner is described for example in WO 91/12079. Thus, salt may be added to the support and released nucleic acid in solution, followed by addition of alcohol which will cause the nucleic acid to precipitate. Alternatively, the salt and alcohol may be added together, or the salt may be omitted. As described above in relation to the cell binding step, any suitable alcohol or salt may be used, and appropriate amounts or concentrations may readily be determined.

Alternative non-specific nucleic acid-binding techniques include the use of detergents as described in WO 96/18731 of Dynal AS (the so-called "DNA Direct" procedure), and the use of chaotropes and a nucleic acid-binding solid phase such as silica particles as described by Akzo N. V. in EP-A-0389063.

Ionic binding of the nucleic acid to the support may be achieved by using a solid support having a charged surface, for example a support coated with polyamines.

The support which is used in the method of the invention may also carry functional groups which assist in the specific or non-specific binding of nucleic acids, for example DNA-binding proteins eg. leucine zippers or histones or intercalating dyes (eg. ethidium bromide or Hoechst 42945) which may be coated onto the support.

Likewise, the support may be provided with binding partners to assist in the selective capture of nucleic acids. For example, complementary DNA or RNA sequences, or DNA binding proteins may be used, or viral proteins binding to viral nucleic acid. The attachment of such proteins to the solid support may be achieved using techniques well known in the art.

A convenient method of precipitating the nucleic acid according to the invention is by adding a precipitant, eg. alcohol, to the mixture containing the support and lysed cells. Thus, an appropriate volume of alcohol, eg. 100% or 96% ethanol, may simply be added to the mixture, and incubated for a time period sufficient to allow the released nucleic acid to become bound to the support. The incubation conditions for this step are not critical and may simply comprise incubating at 5-10 minutes at room temperature. However, the length of time may be varied, and temperature. increased according to choice.

Although not necessary, it may be convenient to introduce one or more washing steps to the isolation method of the invention, for example following the nucleic acid binding step. Any conventional washing buffers or other media may be used. Generally speaking, low to moderate ionic strength buffers are preferred eg. 10 mM Tris-HCl at pH 8.0/10mM NaCl. Other standard washing media, eg. containing alcohols, may also be used, if desired, for example washing with 70% ethanol.

The use of magnetic particles permits easy washing steps simply by aggregating the particles, removing the nucleic acid binding medium, adding the washing medium and reaggregating the particles as many times as required.

Following the nucleic acid isolation process and any optional washing steps which may be desired, the support carrying the bound nucleic acid may be transferred eg. resuspended or immersed into any suitable medium eg. water or low ionic strength buffer. Depending on the support and the nature of any subsequent processing desired, it may or may not be desirable to release the nucleic acid from the support.

In the case of a particulate solid support such as magnetic or non-magnetic beads, this may in many cases be used directly, for example in PCR or other amplifications, without eluting the nucleic acid from the support. Also, for many DNA detection or identification methods elution is not necessary since although the DNA may be randomly in contact with the bead surface and bound at a number of points by hydrogen bonding or ionic or other forces, there will generally be sufficient lengths of DNA available for hybridisation to oligonucleotides and for amplification.

However, if desired, elution of the nucleic acid may readily be achieved using known means, for example by heating, eg. to 65° C. for 5 to 10 minutes, following which the support may be removed from the medium leaving the nucleic acid in solution. Such heating is automatically obtained in PCR by the DNA denaturation step preceding the cycling program.

If it is desired to remove RNA from DNA, this may be achieved by destroying the RNA before the DNA separation step, for example by addition of an RNAase or an alkali such as NaOH.

An advantage of the present invention, is that it is quick and simple to perform, and with an appropriate combination of cell-binding, lysis and nucleic acid binding steps, provides a method which reliably and simply yields isolated nucleic acid in a short period of time, in many cases, less than one hour, or even less than 45 minutes. The simplicity of the method allows for high throughput of samples. Concomitantly, the cell-binding step, results in an enrichment or concentration of the cells, thereby improving the nucleic acid isolation process.

The invention is advantageously amenable to automation, particularly if particles, and especially, magnetic particles are used as the support.

As mentioned above, the method of the invention has particular utility as a preliminary first step to prepare nucleic acid for use in nucleic acid-based detection procedures.

Thus, a further aspect of the present invention is the use of the nucleic acid isolation method as hereinbefore defined in the preparation of nucleic acid for use in a nucleic acid-based target cell detection method.

Alternatively viewed, this aspect of the invention provides a method for detecting the presence or absence of a target cell in a sample, said method comprising:

(a) binding cells in said sample to a solid support to isolate cells from the sample;

(b) lysing the isolated cells;

(c) binding nucleic acid released from said lysed cells to said same solid support; and (d) detecting the presence or absence of nucleic acid characteristic of said target cells within said bound nucleic acid.

As mentioned above, advantageously the bound nucleic acid need not be eluted or removed from the support prior to carrying out the detection step, although this may be performed if desired. Whether or not the nucleic acid is eluted may also depend on the particular method which was used in the nucleic acid binding step. Thus certain nucleic acid-binding procedures will bind the nucleic acid more tightly than others. In the case of DNA-binding using detergents (eg. by DNA Direct) for example, the nucleic acid will elute from the solid support when an elution buffer or other appropriate medium is introduced. Nucleic acid bound by means of a precipitant such as alcohol or a chaotrope will remain more tightly bound and may not elute when placed in a buffer medium, and may require heating to be eluted.

Thus, the support-bound nucleic acid may be used directly in a nucleic acid based detection procedure, especially if the support is particulate, simply by resuspending the support in, or adding to the support, a medium appropriate for the detection step. Either the nucleic acid may elute into the medium, or as mentioned above, it is not necessary for it to elute.

A number of different techniques for detecting nucleic acids are known and described in the literature and any of these may be used according to the present invention. At its simplest the nucleic acid may be detected by hybridisation to a probe and very many such hybridisation protocols have been described (see eg. Sambrook et al., 1989, Molecular Cloning: A Laboratory Manual, 2nd Ed. Cold Spring Harbor Press, Cold Spring Harbor, N.Y.). Most commonly, the detection will involve an in situ hybridisation step, and/or an in vitro amplification step using any of the methods described in the literature for this. Thus, as mentioned, techniques such as LAR, 3SR and the Q-beta-replicase system may be used. However, PCR and its various modifications eg. the use of nested primers, will generally be the method of choice (see eg. Abramson and Myers, 1993, Current Opinion in Biotechnology, 4: 41-47 for a review of nucleic acid amplification technologies).

Other detection methods may be based on a sequencing approach, for example, the minisequencing approach as described by Syvänen and Söderlund, 1990, Genomics, 8: 684-692.

In amplification techniques such as PCR, the heating required in the first step to melt the DNA duplex may release the bound DNA from the support. Thus, in the case of a subsequent detection step, such as PCR, the support bound nucleic acid may be added directly to the reaction mix, and the nucleic acid will elute in the first step of the detection process. The entire isolated support bound nucleic acid sample obtained according to the invention may be used in the detection step, or an aliquot.

The results of the PCR or other detection step may be detected or visualised by many means, which are described in the art. For example the PCR or other amplification products may be run on an electrophoresis gel eg. an ethidium bromide stained agarose gel using known techniques. Alternatively, the DIANA system may be used, which is a modification of the nested primer technique. In the DIANA (Detection of Immobilised Amplified Nucleic Acids) system (see Wahlberg et al., Mol. Cell Probes 4: 285(1990)), the inner, second pair of primers carry, respectively, means for immobilisation to permit capture of amplified DNA, and a label or means for attachment of a label to permit recognition. This provides the dual advantages of a reduced background signal, and a rapid and easy means for detection of the amplified DNA.

The amplified nucleic acid may also be detected, or the result confirmed, by sequencing, using any of the many different sequencing technologies which are now available, eg. standard sequencing, solid phase sequencing, cyclic sequencing, automatic sequencing and minisequencing.

Advantageously, it has been found that isolated cells may be kept in a "cell-binding" buffer according to the invention eg. a salt/alcohol buffer for at least one week at room temperature with no detectable loss of sensitivity in a subsequent nucleic acid detection step. Such stability is an advantage in field situations.

The various reactants and components required to perform the methods of the invention may conveniently be supplied in kit form. Such kits represent a further aspect of the invention.

At its simplest, this aspect of the invention provides a kit for isolating nucleic acid from a sample comprising:

(a) a solid support;
(b) optionally, means for binding cells to said solid support;
(c) means for lysing said cells; and
(d) means for binding nucleic acid released from said lysed cells to said same solid support.

The various means (b), (c) and (d) may be as described and discussed above, in relation to the method of the invention.

A further optional component is (e), means for detecting the presence or absence of nucleic acid characteristic of a target cell within said band nucleic acid. As discussed above, such means may include appropriate probe or primer oligonucleotide sequences for use in hybridisation and/or amplification-based detection techniques.

Optionally further included in such a kit may be buffers, salts, polymers, enzymes etc.

The invention will now be described in more detail in the following non-limiting Examples with reference to the drawings in which:

FIG. 1 shows the results on EtBr-stained agarose gel electrophoresis of the separation of PCR amplification products of DNA obtained according to the invention from cells of 5 cyanobacterial species. Lanes 1 to 7 correspond to samples 1 to 7 as described in Example 1.

EXAMPLE 1

Materials

Sample 1; *Planktothrix rubescens* NIVA-CYA 1, sample 2; *Planktothrix agardhii* NIVA-CYA 29, sample 3; *Planktothrix rubescens* NIVA-CYA 55, sample 4; *Planktothrix mougeotii* NIVA-CYA 56/1, sample 5; *Planktothrix agardhii* NIVA-CYA 116, sample 6; negative control on cell and DNA purification reagents and sample 7; negative control on PCR reagents.

Cell and DNA Isolation Protocol 0.5 ml of water containing approximately $10^5$ cells as mixed with 20 µl beads (1 µg/ml) and 0.5 ml cell binding buffer (isopropanol, 0.75 M $NH_4Ac$) in a microcentrifuge tube. The mixture was incubated at room temperature for 20 minutes, then the tube was placed in a MPC-E magnet (Dynal A.S.) for 2 minutes. The supernatant was carefully removed. 50 µl 4 M GTC, 1% sarkosyl was added and incubated at 65° C. for 10 minutes. Then 200 µl of 96% EtOH was added and the incubation continued for 5 minutes at room temperature. The beads were attracted to the tube wall with the magnet and the supernatant removed. The complex was washed twice with 500 µl 70% EtOH. All of the ethanol was removed and 50 µl water added. To remove residual ethanol the tubes were incubated at 65° C. for 10 minutes with an open lid.

PCR amplification:

The region between the genes coding for RuBisCo large (Rbcl) and small subunit (Rbcs) was amplified. Amplifications were done using the GeneAmp 2400 PCR system (Perkin Elmer) in 50 µl volumes containing 10 pmol primers (CW) 5'CGTAGCTTCCGGTGGTATCCACGT3' (SEQ ID NO: 1) and (DF) 5'GGGCARYTTCCACAKNGTCCA3' (SEQ ID NO: 2), 200 µM KC1, 0.1% Triton X-100, 1 U DynaZyme thermostable DNA polymerase (Finnzymes Oy) and 5 µl of the bead/DNA solution. The PCR program used has an initial denaturation step at 94° C. for 30 seconds, 40° C. for 30 seconds and 72° C. for 2 minutes for 2 cycles, then 94° C. for 30 seconds, 60° C. for 30 seconds and 72° C. for 2 minutes for 40 cycles. Finally, an extension step for 7 minutes was included. By DNA sequencing the amplified fragments were verified to be the region between RuBisCo large (Rbcl) and small (Rbcs) subunit.

Gel:

10 µl of the amplified products from each of samples 1 to 7 were run on a 1.5% EtBr stained agarose gel for 30 minutes at 100 volts. The molecular weight standard was φX 174 HaeIII digested DNA. The results are shown in FIG. 1.

Results:

FIG. 1 clearly shows that the cells from all the samples 1 to 5 could be detected. Based on the PCR results obtained, as visualised on the EtBr stained agarose gel, the detection limit was estimated to be 10-100 cells/ml.

We claim:

1. A method of isolating nucleic acid from a sample of eukaryotic or prokaryotic cells, said method comprising:
   (a) providing a solid support and mixing it with the cell sample and allowing binding of cells in said sample to the solid support to isolate cells from the sample,
   (b) separating the cells bound to the solid support from the remainder of the sample by pipetting or decanting, thereby concentrating the cells,
   (c) lysing the isolated cells, and
   (d) binding nucleic acid released from said lysed cells to a solid support that consists of the same solid support as in step (a); wherein said method further comprises the step of:
   (e) eluting nucleic acid from said same solid support; or
   (f) detecting the nucleic acid bound to the same solid support.

2. The method of claim 1, wherein said nucleic acid is DNA.

3. The method of claim 1, wherein in step (a) the cells are precipitated onto the support using a precipitant.

4. The method of claim 3, wherein the precipitant comprises alcohol and salt.

5. The method of claim 1, wherein in step (a) the cells bind to the support by virtue of cell-binding moieties provided on or in the support.

6. The method of claim 5, wherein said cell-binding moieties permit selective binding of target cells.

7. The method of claim 1, wherein the support comprises magnetic beads.

8. The method of claim 1, wherein in step (c), the cells are lysed using a detergent and a chaotrope.

9. The method of claim 1, wherein in step (c), the cells are lysed using a detergent or a chaotrope.

10. The method of claim 1, wherein in step (d) the nucleic acid is bound non-specifically to the support.

11. The method of claim 10, wherein the nucleic acid is precipitated onto the support using a precipitant.

12. The method of claim 11, wherein the precipitant comprises at least one of alcohol, salt and a detergent.

13. The method of claim 1, wherein in step (d) the nucleic acid binds to the support by virtue of binding partners provided on the support to assist in the selective capture of nucleic acids.

14. The method of claim 1, wherein the solid support is in the form of particles, and wherein in step (a) said sample is mixed with said particulate support, and allowed to stand for a suitable interval of time to allow the cells to bind to the support, following which the support is removed from the remainder of the sample.

15. A method for detecting the presence or absence of a target eukaryotic or prokaryotic cell in a sample, said method comprising:
   (a) providing a solid support and mixing it with the sample and allowing binding of cells in said sample to the solid support to isolate cells from the sample;
   (b) separating the cells bound to the solid support from the remainder of the sample by pipetting or decanting, thereby concentrating the cells,
   (c) lysing the isolated cells;
   (d) binding nucleic acid released from said lysed cells to a solid support that consists of the same solid support as in step (a); and
   (e) detecting the presence or absence of nucleic acid characteristics of said target cells within said bound nucleic acid.

* * * * *